United States Patent [19]

Smith-Lewis et al.

[11] Patent Number: 4,753,890
[45] Date of Patent: Jun. 28, 1988

[54] ANALYTICAL ELEMENT AND METHOD FOR DETERMINATION OF MAGNESIUM IONS

[75] Inventors: Margaret J. Smith-Lewis, Pittsford; John C. Mauck, Rochester; John L. Toner, Webster, all of N.Y.

[73] Assignee: Eastman Kodak Company, Rochester, N.Y.

[21] Appl. No.: 857,219

[22] Filed: Apr. 29, 1986

[51] Int. Cl.$^4$ ..................... G01N 31/22; G01N 33/20
[52] U.S. Cl. .......................................... 436/74; 436/79; 422/56; 422/57; 422/58
[58] Field of Search ............. 436/74, 79; 422/56, 422/57, 58; 534/652

[56] References Cited

U.S. PATENT DOCUMENTS 3,663,525  5/1972  Witterholt et al. ............... 260/149
4,383,043  5/1983  Denney et al. ...................... 436/74
4,503,156  3/1985  Yamazato et al. .................. 436/79

OTHER PUBLICATIONS

Budesinsky et al., *Inorg. Chem*, 10 (2), pp. 313-317 (1971).
Podchainova et al., *Zhur. Analiticheskoi Khimii*, 32(4), pp. 822-832 (1977).
Malevannyi et al., *Tr. Inst. Khim. Ural. Nauchn. Tsentr. Akad. Nauk SSSR*, 30, pp. 55-61 (1974)—Abstract Only.
Malevannyi et al., *Izv. Tomsk. Politrekh. Inst.*, 238, pp. 86-88 (1977)—Abstract Only.
Krupina et al., *Khim. Prom-st., Ser.: Fosfurnaya Prom-st.*, 500, 13-17 (1979)—Abstract Only.
Wizinger et al., *Helv. Chimica Acta.*, 36, pp. 531-536 (1953).
Fung et al., *Chemical Reagents*, 4 (4), pp. 219-222 (1982).
Yu et al., *Analytical Chemistry*, 11 (3), pp. 187-192 (1982).
Yu et al., *Chem. J. of Chinese Universities*, 4 (2), pp. 185-188 (1983).

*Primary Examiner*—Barry S. Richman
*Assistant Examiner*—Jill Johnston
*Attorney, Agent, or Firm*—J. Lanny Tucker

[57] ABSTRACT

An analytical element is used to determine magnesium ions at a pH of from about 8.5 to about 11. This element comprises an absorbent carrier material containing a 1,5-bis(2-hydroxyphenyl)-3-cyanoformazan compound which is substituted in at least one of the 3-, 4- and 5-positions of either phenyl moiety. The substituents are chosen such that their cumulative Hammett-sigma value is greater than about 0.23, provided that none of the substituents is carboxy. The assay is carried out in the presence of a calcium ion chelating agent and a suitable buffer. In preferred embodiments, the cyanoformazan is incorporated in the element in such a manner so as to be isolated from protein molecules which may be encountered in the assay.

21 Claims, 1 Drawing Sheet

ANALYTICAL ELEMENT AND METHOD FOR DETERMINATION OF MAGNESIUM IONS

FIELD OF THE INVENTION

This invention relates to clinical chemistry. More specifically, it relates to an analytical element and method for the determination of magnesium ions.

BACKGROUND OF THE INVENTION

Magnesium in its ionic form is essential to many physiological processes. It is one of the most abundant cations in the body and, next to potassium, it is the most prevalent intracellular ion. It plays a vital role in carbohydrate and lipid metabolism by serving as an activator of adenosine triphosphate (ATP) in the transfer of energy rich phosphate. It is also essential as an activating ion for many enzymes involved in lipid, carbohydrate and protein metabolism. In muscle tissue, magnesium has a significant influence on neuromuscular apparatus.

The amount of magnesium in the body is particularly significant. Decreased levels of magnesium in the body produce muscle irritability which, if not corrected, can result in involuntary muscle spasms and convulsions. On the other hand, increased levels of magnesium can result in a loss of deep tendon reflexes, a loss of touch, temperature and pain sensation, respiratory failure and cardiac arrest.

Therefore, it has been long recognized that for suitable diagnosis and treatment of various ailments, the accurate and rapid measurement of magnesium ions is important. In addition, it is also important in many environmental monitoring programs and manufacturing processes that magnesium be accurately measured.

Colorimetric methods are known for the determination of the concentration of magnesium ions in various fluids, e.g. groundwater, seawater, wastewater, manufacturing liquids and biological fluids. These methods usually involve adding a reagent to the fluid which forms a colored complex with any magnesium ions present. The complex absorbs electromagnetic radiation at a characteristic wavelength different from that of uncomplexed reagent.

The known methods for determining magnesium have various drawbacks. The fluids to be tested often contain various materials which interfere with the complexation of magnesium ions with a complexing dye. For example, proteins and calcium ions present in fluids can also complex with the dye thereby causing an interference.

Hydroxy-substituted cyanoformazan derivatives have been used in the analysis of metal ions in fluids for some time, as described by Budesinsky et al, *Inorg. Chem.*, 10(2), 313–317 (1971) and Podchainova et al, *Zhur. Analiticheskoi Khimii*, 32(4), 822–832 (1977). These references describe the complexation properties of several cyanoformazans with various metal ions. In the Chinese journal *Chemical Reagents*, 4(4), pp. 219–222 (1982), the effect of surfactants on the water-dispersibility of 1,5-bis(2-hydroxy-5-sulfophenyl)-3-cyanoformazan and 1,5-bis(2-hydroxy-5-chlorophenyl)-3-cyanoformazan was evaluated. However, use of these compounds presents problems. Both must be used at relatively high pH, i.e. greater than 11, for greatest sensitivity for magnesium ions. Otherwise, their selectivity for magnesium is low. Further, the 5-sulfophenyl derivative exhibits high background in an assay for magnesium ions.

A recent advance in clinical chemistry was the development of analytical elements useful in dry assays. Examples of such elements are described, for example, in U.S. Pat. Nos. 3,992,158 (issued Nov. 16, 1976 to Przybylowicz et al) and 4,258,001 (issued Mar. 24, 1981 to Pierce et al).

Early attempts to assay liquids for magnesium ions with dry analytical elements were unsuccessful. Known dyes which complex magnesium ions also complex with calcium ions which are often present in liquids to be tested. Further, it was found that proteins adversely affect the assay by complexing with the dyes and biasing the results. Yet it would be desirable to have a dry assay which avoids the problems encountered with both known solution and dry assays.

SUMMARY OF THE INVENTION

The problems noted above are overcome with an analytical element for the determination of magnesium ions comprising an absorbent carrier material containing a 1,5-bis(2-hydroxyphenyl)-3-cyanoformazan substituted in at least one of the 3-, 4- and 5-positions of either phenyl moiety with a substituent such that the cumulative Hammett-sigma value of the substituents is greater than about 0.23, provided that none of the substituents is carboxy, the cyanoformazan being capable of complexing with magnesium ions at a pH of from about 8.5 to about 11.

More particularly, the element comprises a support having thereon, a reagent zone containing a 1,5-bis(2-hydroxyphenyl)-3-cyanoformazan substituted in at least one of the 3-, 4- and 5-positions of either phenyl moiety with a substituent such that the cumulative Hammett-sigma value of the substituents is greater than about 0.23, provided that none of the substituents is carboxy, the cyanoformazan being capable of complexing with magnesium ions at a pH of from about 8.5 to about 11, and a porous zone for accommodating protein molecules provided that said cyanoformazan is incorporated in said element in such a manner so as to be isolated from protein molecules which may be added during an assay.

This invention also provides a method for the determination of magnesium ions comprising the steps of:

A. in the presence of a calcium ion chelating agent and a buffer which is capable of maintaining assay pH within the range of from about 8.5 to about 11, contacting a sample of a liquid suspected of containing magnesium ions with the analytical element described above, and B. detecting the color change resulting from the formation of a complex of the cyanoformazan with magnesium ions.

The present invention provides a rapid and convenient assay for magnesium ions using a dry analytical element which is adaptable for highly automated analytical equipment and procedures. Hence, tedious wet assays are avoided. Within the pH range of from about 8.5 to about 11, assay sensitivity for magnesium is improved and the complexing dye has improved stability. Further, protein interference is minimized with the present invention.

These advantages are obtained by using an element that contains a magnesium ion complexing dye selected from a class of 2-hydroxy-substituted cyanoformazans which form a detectable dye-magnesium ion complex at the specified pH. The assay is carried out in the presence of a calcium ion chelating agent which has a much higher selectivity for calcium ions over magnesium ions, thereby removing the interference from calcium ions. In preferred embodiments, protein interference is eliminated by incorporating the complexing dye in the element so that it is isolated from protein molecules which may be added with the test liquid.

BRIEF DESCRIPTION OF THE DRAWING

The FIGURE is a graphical plot of reflection density vs. concentration of magnesium ions in using the elements of this invention in Example 1 below.

DETAILED DESCRIPTION OF THE INVENTION

Figure 1:
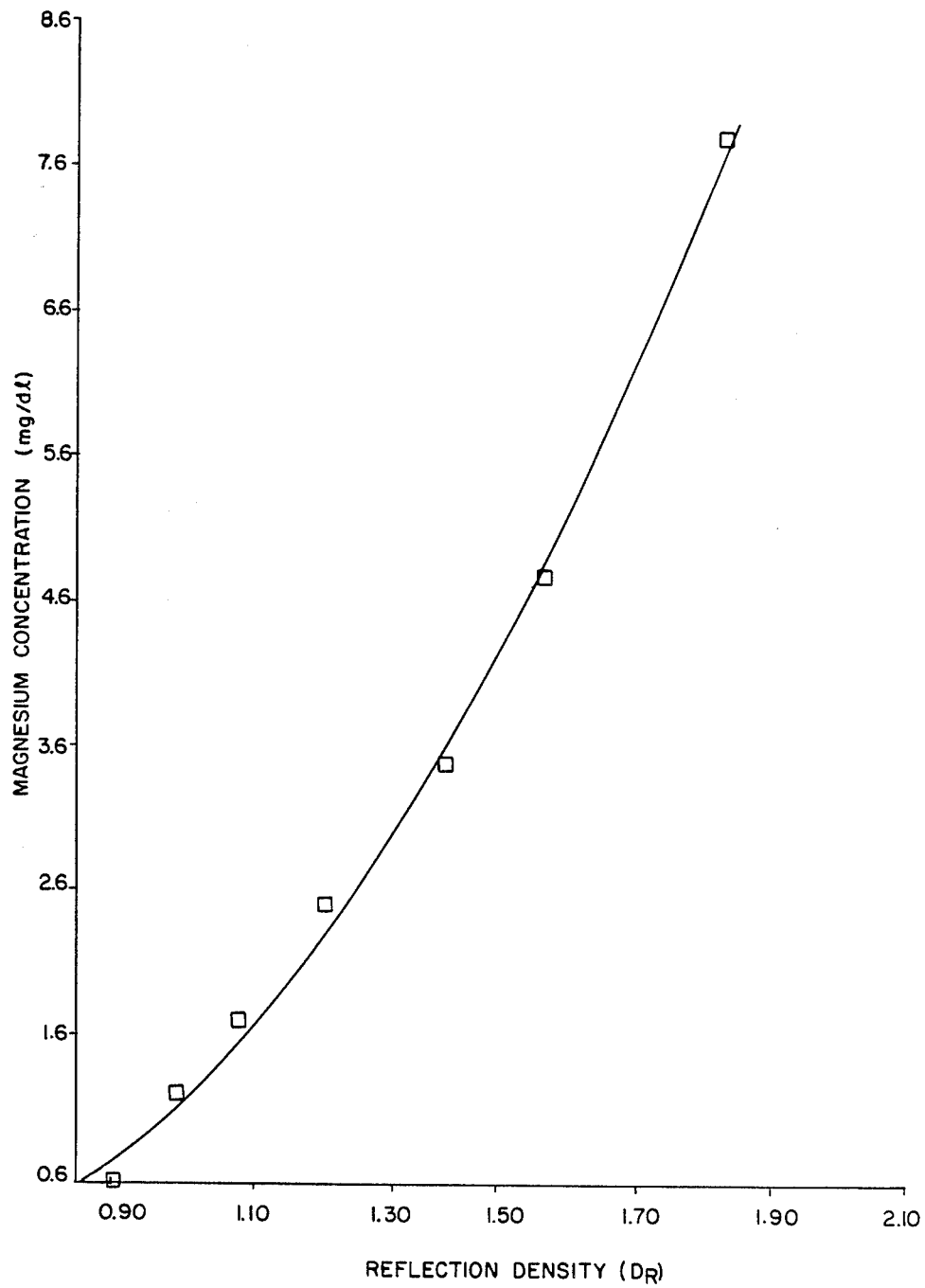

The element of this invention can be used to advantage to assay for magnesium ions in a wide variety of aqueous liquids, e.g. industrial, farm and residential wastewater, food and pharmaceutical processing solutions, food stuffs, groundwater, seawater, biological fluids, etc. The invention can be used to advantage to determine magnesium ions in liquids containing substantially no protein molecules. Alternatively and preferably, the invention is used to determine magnesium ions in various human and animal biological fluids, e.g. whole blood, blood sera and plasma, urine, lymph fluid, spinal fluid, sputum, homogenized tissue, stool secretions, etc. which generally contain protein molecules. The practice of this invention is particularly important for clinical assay of serum or urine.

The compounds useful in the practice of this invention to determine magnesium ions are 1,5-bis(2-hydroxyphenyl)-3-cyanoformazans which are substituted in at least one of the 3-, 4- and 5-positions of either phenyl moiety with a substituent such that the cumulative Hammett-sigma value of the substituents is greater than about 0.23 which is approximately the Hammett-sigma value for a single chloro substituent in either the 3- or 5-position. In a preferred embodiment, the novel compounds of U.S. Ser. No. 857,001 filed on Apr. 29, 1986 by Babb et al, entitled HYDROXY-SUBSTITUTED CYANOFORMAZANS AND THEIR USE IN ANALYTICAL COMPOSITIONS AND METHODS are used. These novel compounds have a cumulative Hammett-sigma value greater than about 0.35. However, none of the substituents is carboxy because dyes having carboxy groups have been found to lack sufficient stability for long term keeping in a dry element. U.S. Ser. No. 857,001 also relates to the use of such compounds in solution assays.

The cyanoformazans described herein must be capable of complexing with magnesium ions at a pH of from about 8.5 to about 11. Such complexing property can be readily evaluated by putting a given compound in a solution buffered to a pH of from about 8.5 to about 11, and observing whether or not a color change occurs when magnesium ions are added to the solution. If a color change occurs, complexation has taken place.

Hammett-sigma values ($\sigma$) are standard values used to predict the electron-withdrawing or electron-donating effect of substituents on phenyl rings. Such values can be calculated according to standard procedures described, e.g. in *Steric Effects in Organic Chemistry*, John Wiley & Sons, Inc., pp. 570–574 (1956) and *Progress in Physical Organic Chemistry*, Vol. 2, Interscience Publishers, pp. 333–339 (1964). Some Hammett-sigma values are listed in the text by March, *Advanced Organic Chemistry: Reactions, Mechanisms, and Structure*, McGraw-Hill Book Company, New York, pp. 238–241 (1968). As defined herein, the cumulative Hammett-sigma value for a cyanoformazan compound is for the substituents in the 3-, 4- and 5-positions of the phenyl rings.

Any substituent, or combination of substituents, can be used on the phenyl rings which will give the desired electronegative effect except carboxy substituents. Generally, the useful substituents are considered more electron-withdrawing than a single chlor group. However, substituents which are less electron-withdrawing than chloro can be used in the appropriate positions as long as they are used with other substituents more electron-withdrawing than chloro which provide the desired cumulative effect.

Representative substituents include halo (fluoro, chloro, bromo, etc.), nitro, sulfamoyl (i.e. $-SO_2NR_1R_2$ wherein $R_1$ and $R_2$ are independently hydrogen, substituted or unsubstituted alkyl of 1 to 12 carbon atoms, e.g. methyl, ethyl, isopropyl, benzyl, dodecyl, chloromethyl, etc., cycloalkyl of 4 to 6 carbon atoms, e.g. cyclobutyl, cyclohexyl, etc. as well as a hydrogen-terminated chain of alkylene or cycloalkylene groups separated by oxy or thio linkages), cyano, substituted or unsubstituted haloalkyl (e.g. mono-, di- or trihaloalkyl wherein the alkyl has from 1 to 12 carbon atoms, e.g. chloromethyl, dibromomethyl, 1,2-dichloroethyl, etc.), carboxamide and substituted or unsubstituted carboxyalkyl (wherein the alkyl has from 1 to 12 carbon atoms as defined above for $R_1$), substituted or unsubstituted sulfoalkyl (wherein the alkyl has from 1 to 12 carbon atoms as defined above for $R_1$), and others known to one of ordinary skill in organic chemistry.

Particularly useful substituents include chloro, sulfomoyl and substituted or unsubstituted sulfoalkyl as defined above. It is also preferred that the cyanoformazans have the same substituents in the 3-, 4- or 5-position of both phenyl rings of the compound. Most preferably, the substituents are in both of either of the 3- or 5-position.

Without intending to limit the scope of this invention, representative useful cyanoformazan compounds include the following compounds listed with their approximate cumulative Hammett-sigma values:

1,5-bis(2-hydroxy-3,5-dichlorophenyl)-3-cyanoformazan, $\sigma$ of about +0.46, 1,5-bis(2-hydroxy-5-sulfamoylphenyl)-3-cyanoformazan, $\sigma$ of about +0.57, 1,5-bis[2-hydroxy-5-(N-n-butylsulfamoyl)phenyl]-3-cyanoformazan, $\sigma$ of about +0.42, 1,5-bis[2-hydroxy-5-(N-n-hexylsulfamoyl)phenyl]-3-cyanoformazan, $\sigma$ of about +0.42, 1,5-bis[2-hydroxy-5-(N-n-octylsulfamoyl)phenyl]-3-cyanoformazan, $\sigma$ of about +0.40, 1,5-bis[2-hydroxy-5-(N-n-dodecylsulfamoyl)phenyl]-3-cyanoformazan, $\sigma$ of about +0.40, 1,5-bis[2-hydroxy-5-(N,N-diethylsulfamoyl)phenyl]-3-cyanoformazan, $\sigma$ of about +0.40, 1,5-bis(2-hydroxy-5-cyanophenyl)-3-cyanoformazan, $\sigma$ of about +0.66, 1,5-bis(2-hydroxy-4-nitrophenyl)-3-cyanoformazan, $\sigma$ of about +0.71, 1,5-bis(2-hydroxy-5-nitrophenyl)-3-cyanoformazan, $\sigma$ of about +0.78, 1,5-bis(2-hydroxy-3-sulfo-5-chlorophenyl)-3-cyanoformazan, $\sigma$ of about +0.32, 1,5-bis-[2-hydroxy-3-chloro-5-(N-n-butylsulfamoyl)-phenyl]-3-cyanoformazan, $\sigma$ of about +0.65, and
1,5-bis-(2-hydroxy-3-methylsulfonylphenyl)-3-cyanoformazan, $\sigma$ of about +0.72.

The first compound in the above list is preferred in the practice of this invention.

The cyanoformazans described herein can be prepared using standard starting materials and the following general procedure: (1) a 2-hydroxyaniline substituted with the appropriate substituent in the 3-, 4- or 5-position is reacted with sodium nitrite in hydrochloric acid, and (2) the resulting diazooxide is reacted with cyanoacetic acid in an azo coupling reaction to provide the cyanoformazan derivative. Detailed preparations of several compounds are provided in copending and commonly assigned U.S. Ser. No. 857,001, noted above.

The method of this invention is practiced with a dry analytical element. The simplest element can be composed of an absorbent carrier material, e.g. a thin sheet of a self-supporting absorbent or bibulous material, such as filter paper or strips, which contains the cyanoformazan described herein. The element can be divided into one or more discrete zones with different reagents incorporated into individual zones of the carrier material. Such elements are known in the art as test strips, diagnostic elements, dip sticks, diagnostic agents and the like.

Useful absorbent carrier materials are insoluble and maintain their structural integrity when exposed to water or biological fluids such as whole blood or serum. Useful elements can be prepared from paper, porous particulate structures, porous polymeric films, cellulose, glass fibers, woven and nonwoven fabrics (synthetic and nonsynthetic) and the like. Useful materials and procedures for making such elements are well known in the art.

A preferred element of this invention comprises a reagent zone containing the cyanoformazan and a porous zone for accommodating protein or other large molecules (i.e. having sufficient porosity for receiving protein or other large molecules). In other words, the porous zone is permeable to protein molecules as that term is used in the art, e.g. in U.S. Pat. No. 4,132,528 (issued Jan. 2, 1979 to Eikenberry et al). One or more cyanoformazan compounds are incorporated into the reagent zone. This zone generally has one or more binder materials, e.g. gelatin, polysaccharides, poly(vinyl alcohol) and other natural and synthetic materials known to one skilled in the art. The porous zone is described in more detail below.

The cyanoformazan described herein is preferably incorporated in the element in such a manner so that it is isolated from protein molecules which may be added with a liquid sample during the assay. This can be accomplished in a number of ways. For example, the cyanoformazan can be immobilized in a reagent zone. Because the cyanoformazan is immobilized, it is not able to migrate into other zones. The reagent zone is substantially impermeable and nonporous to higher molecular materials (e.g. proteins).

Alternatively and most preferably, the cyanoformazan is allowed to migrate in certain zones but is prevented from reaching any protein molecules elsewhere in the element by an interposing diffusion barrier zone. Such a zone keeps protein and other similar large molecules from interacting with the cyanoformazan because it has a lower permeability than the porous zone containing the protein molecules. Yet, the barrier zone must allow diffusion of fluid, magnesium ions and other small molecules. Generally, the cyanoformazan can also migrate through the barrier zone, but it does so at a relatively slow rate. Hence, complexation of magnesium ions and cyanoformazan occurs before migration occurs to any significant extent. Materials for making such zones include hardened gelatin, poly(isopropylacrylamide), poly(vinyl pyrrolidone) and other materials known in the art.

Organic solvents can also be incorporated in the reagent zone with the cyanoformazan. It has been unexpectedly found that, while the use of such solvents is not essential, it is preferred in order to increase the sensitivity of the assay even further. Useful organic solvents generally include any solvent in which a cyanoformazan is soluble, e.g. diethyl lauramide, dioctylphenylphosphonate and others known in the art.

The assay of this invention is carried out at a pH of from about 8.5 to about 11 using one or more suitable buffers, e.g. 2-(N-cyclohexylamino)ethane sulfonic acid (CHES), N,N-bis(2-hydroxyethyl)glycine (bicine), 3-(cyclohexylamino)-1-propane sulfonic acid (CAPS), L-arginine, and others known in the art, e.g. as reported by Good et al in *Biochem.*, 5, 467 (1966), and *Anal. Biochem.*, 104, 300 (1980). The buffer can be added to the test sample prior to the assay or added to the element as a separate fluid. Generally, the buffer is incorporated in one or more zones of the element. Preferably, the buffer is in the reagent zone. More preferably, the assay is carried out at a pH of from about 9 to about 10.

The assay of this invention is also carried out in the presence of a calcium ion chelating agent. This agent has a high affinity for calcium ions over magnesium ions. Generally, the binding constant of the chelating agent toward calcium is at least two orders of magnitude greater than the binding constant of the cyanoformazan compound toward calcium.

Useful calcium ion chelating agents can be readily determined by a skilled worker in the art with a simple test. Thus test comprises: (1) observing the spectrum of a solution of cyanoformazan alone, (2) adding a known quantity of magnesium ions and observing the spectral shift, (3) observing any spectral shift in a solution of cyanoformazan and calcium ions, (4) adding a test compound thought to be a calcium ion chelating agent to solution 3 and observing any spectral shift, and (5) putting the cyanoformazan, magnesium ions and the test compound together and observing any spectral shift. If the spectra in steps (1) and (4) are identical and the spectral shifts in steps (2) and (5) are identical, the test compound is a suitable calcium ion chelating agent.

Representative calcium ion chelating agents include 1,2-bis(o-aminophenoxy)ethane-N,N,N',N'-tetraacetic acid (also known as BAPTA), and other compounds described by Tsien in *Biochem.*, 19, pp. 2396–2404 (1980).

The calcium ion chelating agent can be added to the test sample prior to the assay, or added to the element as a separate fluid prior to, simultaneously with or subsequently to addition of the test fluid during the assay. Preferably, the calcium ion chelating agent is incorporated in one or more zones of the element. Alternatively and preferably, it is incorporated in one or more binder materials (as described above) in a separate chelating agent zone located between the reagent zone and the porous spreading zone. In a preferred embodiment, this chelating agent zone can also be the diffusion barrier zone described above.

The element of this invention can contain one or more porous zones which are capable of absorbing and transporting a sample of liquid applied to the element. These zones are also preferably capable of spreading the liquid sample and accommodating protein molecules which may be added with the test sample. Such zones can be composed of any of a number of porous materials, including paper, porous particulate structures, cellulose, porous polymeric films, glass fibers, woven and nonwoven fabrics (synthetic and nonsynthetic) and the like. Useful materials and procedures for making such elements are well known in the art.

Particularly useful spreading zones are prepared from fibrous or non-fibrous materials or mixtures of either or both as described in U.S. Pat. Nos. 4,292,272 (issued Sept. 29, 1981 to Kitajima et al), 3,992,158 (noted above), 4,258,001 (noted above) and 4,430,436 (issued Feb. 7, 1984 to Koyama et al) and Japanese Patent Publication 57(1982)-101760 (published June 24, 1982).

The zones are optionally carried on a separate support. Such a support can be any suitable dimensionally stable, and preferably, nonporous and transparent (i.e. radiation transmissive) material which transmits electromagnetic radiation of a wavelength between about 200 and about 900 nm. A support of choice for a particular element should be compatible with the intended mode of detection (fluorescence, transmission or reflectance spectroscopy). Useful supports can be prepared from paper, metal foils, polystyrene, polyesters [e.g. poly(ethylene terephthalate)], polycarbonates, cellulose esters (e.g. cellulose acetate), etc.

In the elements of this invention, the cyanoformazan derivative is generally present in an excess of that amount generally needed to complex with all magnesium ions in a sample. Generally, the coverage of a cyanoformazan compound is at least about 0.1, and preferably from about 0.2 to about 0.8, g/m². The calcium ion chelating agent is present in an amount sufficient to substantially eliminate interference by calcium ions in the assay. Generally, the chelating agent is present in a coverage of at least about 0.1, and preferably from about 0.4 to about 8, g/m². The optional organic solvent can be used in a suitable amount to dissolve the cyanoformazan. Other reagents and materials (e.g. buffers, binders, surfactants, etc.) are present in coverages within the skill of a worker in the art.

The element can also contain one or more additional zones, subbing, adhesive, etc. which facilitate coating and handling operations but which do not adversely affect the assay.

The zones of the element can be separate regions in one or more layers. Alternatively and preferably, each zone is a separately coated layer superposed on the support or other layers.

A particularly preferred element of this invention comprises a support having thereon, in order, a reagent layer containing a cyanoformazan described herein, a diffusion barrier layer containing a calcium ion chelating agent described herein distributed in a hardened binder material, and a porous spreading layer for accommodating protein molecules, the element further comprising, in one or more of the layers, a buffer which is capable of maintaining the element at a pH of from about 8.5 to about 11 during an assay.

The assay of this invention can be manual or automated. In general, magnesium ion determination is made by taking the element from a supply roll, chip packet or other source and physically contacting it with a sample (e.g. 1-200 µl) of the liquid to be tested so that the sample is mixed with the reagents in the element. Such contact can be accomplished in any suitable manner, e.g. dipping or immersing the element into the sample or, preferably, by spotting the element by hand or machine with one or more drops of the sample with a suitable dispensing means so that the liquid sample mixes with the reagents within the element.

Determination of magnesium ions is achieved by measuring the amount of dye density resulting from complexation of the cyanoformazan compound with the magnesium ions in the test sample.

In the following examples illustrating the practice of this invention, the materials used were obtained from the following sources: TRITON X-100 and X-405 nonionic surfactants from Rohm and Haas (Philadelphia, Pa., U.S.A.), bovine serum albumin from Miles Laboratories (Elkhart, Ind., U.S.A.), cyclohexylaminoethane sulfonic acid (CHES), from Sigma Chemical Co. (St. Louis, Mo., U.S.A.), ALKANOL XC buffer from DuPont (Wilmington, Del., U.S.A.), ESTANE polyurethane resin from B. F. Goodrich (Cleveland, Ohio, U.S.A.), poly(vinylpyrrolidone) from GAF Corp. (New York, N.Y., U.S.A.), and the remainder from Eastman Kodak Company (Rochester, N.Y., U.S.A.).

EXAMPLE 1

Determination of Magnesium Ions

An element of the present invention was prepared having the following format and components and used to determine magnesium ions.

| | | |
|---|---|---|
| Spreading Layer | Poly(vinyltoluene-co-p-t-butylstyrene-co-methacrylic acid) beads | 100-200 g/m² |
| | Poly(N—isopropylacrylamide) adhesive | 0.1-20 g/m² |
| | TRITON X-100 surfactant | 0.05-2.5 g/m² |
| Subbing Layer | Poly(vinylpyrrolidone) | 0.1-3 g/m² |
| Diffusion Barrier Layer | Gelatin (hardened) | 1-10 g/m² |
| | TRITON X-100 surfactant | 0.2-2.5 g/m² |
| | 1,2 Bis(o-aminophenoxy)ethane-N,N,N',N—tetraacetic acid, sodium salt(BAPTA) | 0.1-8 g/m² |
| Reagent Layer | Gelatin | 3-20 g/m² |
| | TRITON X-100 surfactant | 0.2-2.5 g/m² |
| | 2-(N—cyclohexylamino)ethane sulfonic acid buffer (pH 9.5) | 2-15 g/m² |
| | 1,5-Bis(2-hydroxy-3,5-dichlorophenyl)-3-cyanoformazan | 0.1-1 g/m² |
| | Diethyl lauramide solvent | 0.2-20 g/m² |
| | ALKANOL XC surfactant | 0.05-2 g/m² |
| / / / | Poly(ethylene terephthalate) Support / / / / |  |

Elements were contacted with 10 µl samples of calibrator fluids containing magnesium ions (0.6-7.8 mg/dl) and then incubated at 37° C. The reflection density of the resulting magnesium-cyanoformazan complex was measured in each element using a standard spectrophotometer at 630 nm after about 5 minutes. The resulting data indicate that magnesium ions were accurately measured using the elements of the present invention. The FIGURE is a calibration curve showing the densities of various amounts of magnesium ions according to this invention.

EXAMPLES 2–5

Comparison of Placement of Cyanoformazan Compound

Elements of the invention were prepared as that described in Example 1 except different cyanoformazan compounds were used. The elements contained the following compounds:

Example 2

1,5-bis[2-hydroxy-5-(N,N-diethylsulfamoyl)phenyl]-3-cyanoformazan

Example 3

1,5-bis[2-hydroxy-5-(N-n-butylsulfamoyl)phenyl]-3-cyanoformazan

Example 4

1,5-bis[2-hydroxy-5-(N-n-hexylsulfamoyl)phenyl]-3-cyanoformazan,

Example 5

1,5-bis[2-hydroxy-5-(N-n-octylsulfamoyl)phenyl]-3-cyanoformazan.

Control elements were prepared like each of the elements noted above but with the cyanoformazan compound located in the spreading layer instead of the reagent layer.

All of the elements (including Example 1 element) were contacted with 10 μl samples of calibrator fluids containing magnesium ions (0.6–7.8 mg/dl) and about 7–10 g/dl of protein, and evaluated as described in Example 1. It was observed that the Control elements exhibited a high positive bias due to the presence of protein and its binding of the cyanoformazan. The protein bias of the Control elements was clinically unacceptable (i.e. greater than 1 mg/dl). The protein bias of the elements of this invention were significantly lower in absolute value. The protein bias data are listed in Table I below. Protein bias is determined by using the following equation:

Bias = [Test$_{(protein=10\ g/dl)}$ − Reference$_{(protein=10\ g/dl)}$] −

[Test$_{(protein=7\ g/dl)}$ − Reference$_{(protein=7\ g/dl)}$]

TABLE I

| Element | Protein Bias (mg/dl) Invention | Control |
|---|---|---|
| 1 | −0.21 | +1.0 |
| 2 | −0.44 | +1.16 |
| 3 | −0.54 | +2.03 |
| 4 | −0.52 | +2.22 |
| 5 | −0.54 | +1.35 |

EXAMPLES 6–8

Effect of the Use of Organic Solvent

Several elements of the present invention were prepared like that described in Example 1 using different organic solvents in the reagent layer. Example 6 contained dioctylphenylphosphonate as the organic solvent while Example 7 contained diethyl lauramide. Another element (Example 8) was prepared like the others but without an organic solvent.

The elements were tested as described in Example 1 and the results are shown in Table II below. It is clear from the data that all of the elements were sensitive to magnesium ions. However, the use of the organic solvents in Examples 6 and 7 improved the sensitivity even further. The $\Delta D_R$ (i.e. density range) was obtained by subtracting the $D_R$ readings taken at low magnesium ion concentration (0.6 mg/dl) from those taken at high magnesium ion concentration (7.8 mg/dl).

TABLE II

| Element | $\Delta D_R$ |
|---|---|
| 6 | 0.73 |
| 7 | 1.02 |
| 8 | 0.52 |

EXAMPLES 9 & 10

Alternative Elements of the Invention

Elements of the present invention were prepared and tested as described in Example 1 above except that the spreading layer was prepared using the following composition:

EXAMPLE 9 titanium dioxide (10–100 g/m$^2$, cellulose acetate (3–12 g/m$^2$), TRITON X-405 surfactant (0.5–3 g/m$^2$), BRIJ 78 surfactant (0.2–2 g/m$^2$) and ESTANE polyurethane resin (1–5 g/m$^2$).

EXAMPLE 10 same as Example 9 except barium sulfate was used in place of titanium dioxide.

The results of the assays carried out with these elements are shown in Table III below. Both elements were acceptable for determining magnesium ions in a sensitive and precise manner.

TABLE III

| Element | Precision* (mg/dl) | $\Delta D_R$** |
|---|---|---|
| 9 | 0.1 | 0.70 |
| 10 | 0.09 | 0.80 |

*Standard deviations determined by standard statistical methods.
**Determined as described for Examples 6–8.

EXAMPLE 11

Effect of Calcium Ion Chelating Agent

Elements like that described in Example 1 were prepared with (Example 11) and without (Control) calcium ion chelating agent (BAPTA). Each element was tested with each of three fluids (A, B and C) containing 0, 10 mg/dl calcium ions and 10 mg/dl magnesium ions, respectively. The results of the tests are presented in Table IV below. These results show that the element of this example exhibited no density change when calcium ions were added to the element. Yet that element showed a density change when magnesium ions were added to it. The Control element, however, showed a density shift when either calcium or magnesium ions were added, indicating that calcium ions acted as an interferent in the assay.

TABLE IV

| Element | $\Delta D_{R\ (Ca\#)}$* | $\Delta D_{R\ (Mg\#)}$** |
|---|---|---|
| Example 11 | −0.01 | 0.70 |

TABLE IV-continued

| Element. | Δ $D_{R(Ca\#)}$* | Δ $D_{R(Mg\#)}$** |
|---|---|---|
| Control | +0.22 | 0.34 |

*$D_R$ (Fluid B) - $D_R$ (Fluid A)
**$D_R$ (Fluid C) - $D_R$ (Fluid A)

The invention has been described in detail with particular reference to preferred embodiments thereof, but it will be understood that variations and modifications can be effected within the spirit and scope of the invention.

We claim:

1. An analytical element for the determination of magnesium ions comprising an absorbent carrier material containing a 1,5-bis(2-hydroxyphenyl)-3-cyanoformazan substituted in at least one of the 3-, 4- and 5-positions of either phenyl moiety with a substituent such that the cumulative Hammett-sigma value of said substituents is greater than about 0.23, provided that none of said substituents is carboxy, whereby said cyanoformazan is capable of complexing with magnesium ions at a pH of from about 8.5 to about 11,
the element further comprising a buffer which is capable of maintaining said element at a pH of from about 8.5 to about 11 during an assay.

2. The element of claim 1 further comprising a calcium ion chelating agent present in an amount sufficient to substantially eliminate calcium ion interference.

3. An analytical element for the determination of magnesium ions comprising a support having thereon,
a reagent zone containing a 1,5-bis(2-hydroxyphenyl)-3-cyanoformazan substituted in at least one of the 3-, 4- and 5-positions of either phenyl moiety with a substituent such that the cumulative Hammett-sigma value of said substituents is greater than about 0.23, provided that none of said substituents is carboxy, whereby said cyanoformazan is capable of complexing with magnesium ions at a pH of from about 8.5 to about 11, and
a porous zone free of said cyanoformazan for accommodating protein molecules
provided that said cyanoformazan is incorporated in said element in such a manner so as to be isolated from protein molecules which may be added during an assay,
the element further comprising a buffer which is capable of maintaining said element at a pH of from about 8.5 to about 11 during an assay.

4. The element of claim 3 wherein said cyanoformazan is immobilized in said reagent zone.

5. The element of claim 3 wherein the cumulative Hammett-sigma value of said cyanoformazan substituents is greater than about 0.35.

6. The element of claim 3 further comprising a diffusion barrier zone between said spreading and reagent zones.

7. The element of claim 3 wherein said cyanoformazan is selected from the group consisting of:
1,5-bis(2-hydroxy-3,5-dichlorophenyl)-3-cyanoformazan,
1,5-bis(2-hydroxy-5-sulfamoylphenyl)-3-cyanoformazan,
1,5-bis[2-hydroxy-5-(N-n-butylsulfamoyl)phenyl]-3-cyanoformazan,
1,5-bis[2-hydroxy-5-(N-n-hexylsulfamoyl)phenyl]-3-cyanoformazan,
1,5-bis[2-hydroxy-5-(N-n-octylsulfamoyl)phenyl]-3-cyanoformazan,
1,5-bis[2-hydroxy-5-(N-dodecylsulfamoyl)phenyl]-3-cyanoformazan,
1,5-bis[2-hydroxy-5-(N,N-diethylsulfamoyl)phenyl]-3-cyanoformazan,
1,5-bis(2-hydroxy-5-cyanophenyl)-3-cyanoformazan,
1,5-bis(2-hydroxy-4-nitrophenyl)-3-cyanoformazan,
1,5-bis(2-hydroxy-5-nitrophenyl)-3-cyanoformazan,
1,5-bis(2-hydroxy-2-sulfo-5-chlorophenyl)-3-cyanoformazan,
1,5-bis-[2-hydroxy-3-chloro-5-(N-butylsulfamoyl)-phenyl]-3-cyanoformazan, and
1,5-bis-(2-hydroxy-3-methylsulfonylphenyl)-3-cyanoformazan.

8. The element of claim 3 further comprising an organic solvent in said reagent zone.

9. The element of claim 3 further comprising a calcium ion chelating agent present in an amount sufficient to substantially eliminate calcium ion interference.

10. The element of claim 9 wherein said calcium ion chelating agent is 1,2-bis(o-aminophenoxy)ethane-N,N,N',N'-tetraacetic acid or a salt thereof.

11. The element of claim 3 wherein said cyanoformazan is substituted with one or more substituents selected from the group consisting of halo, sulfamoyl, cyano, substituted or unsubstituted haloalkyl, carboxamide, substituted or unsubstituted carboxyalkyl, and substituted or unsubstituted sulfoalkyl.

12. The element of claim 11 wherein said calcium ion chelating agent is 1,2-bis(o-aminophenoxy)ethane-N,N,N',N'-tetraacetic acid or a salt thereof and said cyanoformazan is 1,5-bis(2-hydroxy-3,5-dichlorophenyl)-3-cyanoformazan.

13. An analytical element for the determination of magnesium ions comprising a support having thereon, in order,
a reagent layer containing a 1,5-bis(2-hydroxyphenyl)-3-cyanoformazan substituted in at least one of the 3-, 4- and 5-positions of either phenyl moiety with a substituent such that the cumulative Hammett-sigma value of said substituents is greater than about 0.23, provided that none of said substituents is carboxy, whereby said cyanoformazan is capable of complexing with magnesium ions at a pH of from about 8.5 to about 11, and
a diffusion barrier layer containing a calcium ion chelating agent distributed in a hardened binder material, said agent present in an amount to substantially eliminate calcium ion interference, and
a porous spreading layer free of said cyanoformazan for accommodating protein molecules,
said element further comprising, in one or more of said layers, a buffer which is capable of maintaining said element at a pH of from about 8.5 to about 11 during an assay.

14. A method for the determination of magnesium ions comprising the steps of:
A. in the presence of a calcium ion chelating agent sufficient to substantially eliminate calcium ion interference and a buffer which is capable of maintaining assay pH within the range of from about 8.5 to about 11, contacting a sample of a liquid suspected of containing magnesium ions with an analytical element comprising an absorbent carrier material, containing a 1,5-bis(2-hydroxyphenyl)-3-cyanoformazan substituted in at least one of the 3-, 4- and 5-positions of either phenyl moiety with a substituent such that the cumulative Hammett-sigma value of said substituents is greater than about 0.23, provided that none of said substituents is carboxy, whereby said cyanoformazan is capable of complexing with magnesium ions at a pH of from about 8.5 to about 11, and B. detecting the color change resulting from the formation of a complex of said cyanoformazan with magnesium ions.

15. The method of claim 14 wherein said liquid sample contains substantially no protein.

16. A method for the determination of magnesium ions comprising the steps of:

A. in the presence of a calcium ion chelating agent sufficient to substantially eliminate calcium ion interference and a buffer which is capable of maintaining assay pH within the range of from about 8.5 to about 11, contacting a sample of a liquid suspected of containing magnesium ions with an analytical element comprising a support having thereon, a reagent zone containing a 1,5-bis(2-hydroxyphenyl)-3-cyanoformazan substituted in at least one of the 3-, 4- and 5-positions of either phenyl moiety with a substituent such that the cumulative Hammett-sigma value of said substituents is greater than about 0.23, provided that none of said substituents is carboxy, whereby said cyanoformazan is capable of complexing with magnesium ions at a pH of from about 8.5 to about 11, and a porous zone free of said cyanoformazan for accommodating protein molecules provided that said cyanoformazan is incorporated in said element in such a manner so as to be isolated from protein molecules which may be added during an assay, and B. detecting the color change resulting from the formation of a complex of said cyanoformazan with magnesium ions.

17. The method of claim 16 carried out at a pH of from about 9 to about 10.

18. The method of claim 16 wherein said liquid sample is serum of urine.

19. The method of claim 16 wherein said calcium ion chelating agent is in said element.

20. The method of claim 16 wherein said buffer is in said element reagent zone.

21. The method of claim 16 wherein said calcium ion chelating agent is 1,2-bis(o-aminophenoxy)ethane-N,N,N',N'-tetraacetic acid or a salt thereof and said cyanoformazan is 1,5-bis(2-hydroxy-3,5-dichlorophenyl)-3-cyanoformazan.

* * * * *